United States Patent [19]

Richardson

[11] Patent Number: 4,623,660

[45] Date of Patent: Nov. 18, 1986

[54] TRIPHENYLALKENE DERIVATIVES

[75] Inventor: Dora N. Richardson, Macclesfield, England

[73] Assignee: Imperial Chemical Industries PLC, London, England

[21] Appl. No.: 99,750

[22] Filed: Dec. 3, 1979

Related U.S. Application Data

[63] Continuation of Ser. No. 932,934, Aug. 11, 1978, abandoned.

[30] Foreign Application Priority Data

Aug. 22, 1977 [GB] United Kingdom ................ 7725093
Jan. 27, 1978 [GB] United Kingdom ................... 783364

[51] Int. Cl.[4] .................. A61K 31/135; A61K 31/205
[52] U.S. Cl. ............................... 514/514; 260/501.18; 514/428; 514/648; 548/575; 549/419; 564/324
[58] Field of Search .................... 260/570 R; 424/330; 564/324; 548/575; 549/419

[56] References Cited

U.S. PATENT DOCUMENTS

| | | | |
|---|---|---|---|
| 3,250,767 | 5/1966 | Beneze | 260/570 X |
| 3,493,606 | 2/1970 | Richardson | 260/570 |
| 3,576,874 | 4/1971 | Fried et al. | 260/570 |
| 3,721,712 | 3/1973 | Palopoli et al. | 260/570 |

FOREIGN PATENT DOCUMENTS 1064629  4/1967  United Kingdom ................ 260/570

OTHER PUBLICATIONS

Jordan et al., "Journal Endrcr.", vol. 75, pp. 305–316 (1977).

Primary Examiner—Robert V. Hines
Attorney, Agent, or Firm—Cushman, Darby & Cushman

[57] ABSTRACT

The disclosure relates to 1-p-aminoalkoxy phenyl-1-p-hydroxyphenyl-2-phenylalk-1-ene derivatives, processes for their manufacture and pharmaceutical compositions containing them. The compounds possess anti-oestrogenic activity and are useful in the treatment of anovulatory infertility and the breast tumors. Representative of the compounds disclosed is 1-(p-$\beta$-dimethylaminoethoxyphenyl)-trans-1-p-hydroxyphenyl-2-p-tolylbut-1-ene.

7 Claims, No Drawings

TRIPHENYLALKENE DERIVATIVES

This is a continuation of application Ser. No. 932,934, filed Aug. 11, 1978, now abandoned.

This invention relates to triphenylalkene derivatives which possess anti-oestrogenic activity.

It is known from J. Reprod. Fert. (1967), 13, 101 that 1-(p-β-dimethylaminoethoxyphenyl)trans-1,2-diphenylbut-1-ene (tamoxifen) shows anti-oestrogenic activity in rats and, in this species, is weakly and atypically oestrogenic. It is also known from Xenobiotica (1973), 3, 693 that 1-(p-β-dimethylaminoethoxyphenyl)-trans-1-p-hydroxyphenyl-2-phenylbut-1-ene is a major metabolite of tamoxifen in the dog, but the pharmacological properties of this compound have not been described.

We have now found that a series of 1,1,2-triphenylalkene derivatives, in which one of the phenyl radicals in the 1-position bears a hydroxy group, show anti-oestrogenic activity of the same order as that shown by tamoxifen, but in contrast to the oestrogenic activity expected in a hydroxy compound of this type, the present compounds show only the weak and atypical oestrogenic activity also shown by tamoxifen. Further, the above properties are shown by both the cis- and trans-isomers of the present compounds whereas the cis-isomer of tamoxifen behaves like a conventional oestrogen.

According to the invention there is provided an alkene derivative of the formula:

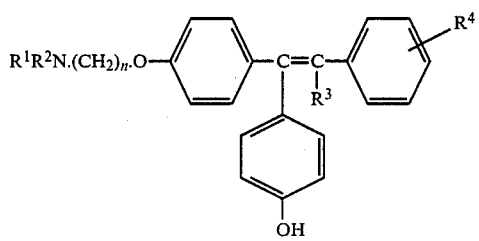

I wherein either $R^1$ is a hydrogen atom or a lower alkyl radical and $R^2$ is a lower alkyl radical, or $R^1$ and $R^2$ are joined together with the adjacent nitrogen atom to form a heterocyclic radical; $R^3$ is a halogen atom or a lower alkyl radical; $R^4$ is a hydrogen or halogen atom, or a hydroxy or lower alkyl radical, or is the buta-1,3-dienyl radical such that together with the benzene ring it forms a naphthyl radical, and n is 2,3,4,5 or 6, or a pharmaceutically acceptable acid addition salt thereof, but excluding 1-(p-β-dimethylaminoethoxyphenyl)-1-p-hydroxyphenyl-2-phenylbut-1-ene and the pharmaceutically acceptable acid addition salts thereof.

As indicated above, a compound of the invention can exist in the form of a cis or a trans isomer in which the designation cis or trans refers to the relative positions of the hydroxyphenyl radical and the phenyl radical bearing the group $R^4$ about the double bond. The cis and trans isomers may be distinguished by the magnetic resonance signals of the protons in the —OCH$_2$— group of the —O(CH$_2$)$_n$NR$^1$R$^2$ side-chain, the signals of these protons in the cis isomers occurring at lower field than of those in the corresponding trans isomers. This invention includes both cis and trans isomers and mixtures thereof which possess the above properties, it being a matter of common general knowledge how to separate cis and trans isomers and how to determine their anti-oestrogenic and oestrogenic activity.

A particularly suitable value for $R^1$, $R^2$, $R^3$ or $R^4$ when it is a lower alkyl radical is, for example, an alkyl radical of 1-4 carbon atoms, for example a methyl, ethyl, n-propyl, isopropyl or a butyl radical.

A particularly suitable value for $R^1$ and $R^2$ when they are joined together with the adjacent nitrogen atom to form a heterocyclic radical is, for example, a 5- or 6-membered nitrogen-containing heterocyclic radical optionally including an oxygen or sulphur atom as a second hetero-atom, for example a pyrrolidino, piperidino or morpholino radical.

A particularly suitable value for $R^3$ or $R^4$ when it is a halogen atom is, for example, a fluorine chlorine or bromine atom.

A particularly suitable salt is, for example, a hydrochloride, sulphate, phosphate, acetate, tartrate or citrate.

A preferred compound of the invention has formula I given above wherein $R^1$ and $R^2$ are both the same lower alkyl radical, preferably the methyl radical, wherein $R^3$ is a lower alkyl radical, preferably the ethyl radical, wherein $R^4$ is a halogen atom or a lower alkyl radical, preferably the fluorine, chlorine or bromine atom or the methyl or ethyl radical, and especially such a radical in the 4-position, and wherein n is 2 or 3, preferably 2, or is a pharmaceutically-acceptable acid-addition salt thereof.

A second preferred compound of the invention has formula I given above wherein $R^1$ and $R^2$ are both the same lower alkyl radical, preferably the methyl or ethyl radical and especially the methyl radical, wherein $R^3$ is a lower alkyl radical, preferably the methyl, ethyl or n-propyl radical, wherein $R^4$ is hydrogen, and wherein n is 3, 4 or 5, or is a pharmaceutically-acceptable acid-addition salt thereof.

Particular compounds of the invention are set out in the Examples, and preferred compounds are 1-(p-β-dimethylaminoethoxyphenyl)-trans-1-p-hydroxyphenyl-2-p-tolylbut-1-ene, 1-(p-β-dimethylaminoethoxyphenyl)-cis-1-p-hydroxyphenyl-2-p-tolylbut-1-ene, 1-(p-dimethylaminoethoxyphenyl)-trans-1-p-hydroxyphenyl-2-p-chlorophenylbut-1-ene, 1-(p-β-dimethylaminoethoxyphenyl)-cis-1-p-hydroxyphenyl-2-p-chlorophenylbut-1-ene, 1-(p-β-dimethylaminoethoxyphenyl)-trans-1-p-hydroxyphenyl-2-p-fluorophenylbut-1-ene and 1-(p-β-dimethylaminoethoxyphenyl)-cis-1-p-hydroxypheny-2-p-fluorophenylbut-1-ene.

A compound of formula I may be obtained by the processes which are applicable to the manufacture of analogous compounds. Thus, for example, an alkanol of the formula:

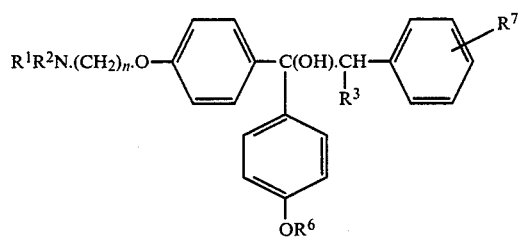

wherein $R^1$, $R^2$, $R^3$ and n have the meanings stated above, wherein $R^6$ is a hydrogen atom or a radical displaceable with acid, for example, a 2-tetrahydropyranyl or methoxymethyl radical, and $R^7$ is a hydrogen or halogen atom, or a lower alkyl radical, or the buta-1,3- dienyl radical, or a radical of the formula R⁶O—, is dehydrated with an acid, for example hydrochloric acid, conveniently in a solvent, for example ethanol, at a temperature of from 20° C. to 80° C.

The alkene derivative so obtained may be in the form of a mixture of the cis and trans isomers. If desired, the individual isomers may be obtained by fractional crystallisation of the mixture, or by chromatography.

The starting material of formula II may be obtained by reacting a bromobenzene derivative of the formula:

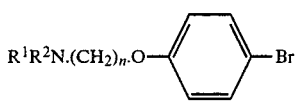

wherein $R^1$, $R^2$ and n have the meanings stated above with a desoxybenzoin derivative of the formula:

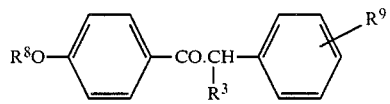

wherein $R^3$ has the meaning stated above, wherein $R^8$ is a protecting group, for example a 2-tetrahydropyranyl radical or a benzyl radical, and $R^9$ is a hydrogen or a halogen atom, or a lower alkyl radical, or the buta-1,3-dienyl radical, or a radical of the formula $R^8O$—, in the presence of an alkyl lithium compound, for example, n-butyl-lithium, followed by removal of the protecting group if desired; or by reacting an excess of a Grignard reagent of the formula:

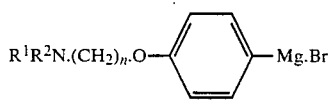

with a desoxybenzoin derivative of the formula:

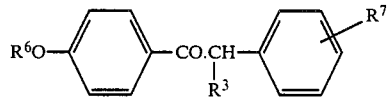

Alternatively, a Grignard reagent of the formula:

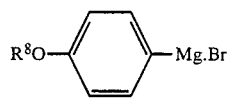

may be reacted with a desoxybenzoin derivative of the formula:

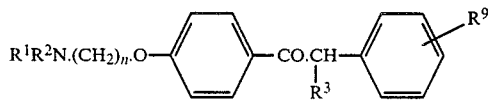

followed by removal of the protecting group if desired.

The anti-oestrogenic activity of a compound of formula I has been demonstrated by its effect in preventing implantation of the fertilised ovum when administered orally to rats on day 4 of pregnancy. In this test, each of the compounds showed substantial activity at a dose of 0.2 mg./kg. and a preferred compound showed activity at a dose of 0.025 mg./kg. Anti-oestrogenic activity can also be demonstrated by inhibition of oestradiol-induced vaginal cornification in ovariectomised rats.

The weak oestrogenic activity of a compound of formula I has been demonstrated by its effect in producing cornified vaginal smears in spayed rats when administered orally once daily for 3 days. In this test, each of the compounds showed oestrogenic activity only at a dose substantially greater than that required to produce anti-oestrogenic effects.

A compound with the above pharmacological properties is of value in the treatment of the same conditions in whch tamoxifen is beneficial, in particular, in the treatment of anovulatory infertility and in the treatment of breast tumours.

When used to produce an anti-oestrogenic effect in warm blooded animals, a typical daily dose is from 0.05 to 1 mg./kg. administered orally, or by injection. In man this is equivalent to an oral dose of from 5-80 mg./day. In use, tamoxifen has been administered orally at doses of from 20-80 mg./day for the treatment of anovulatory infertility, and at doses from 10-40 mg./day for the treatment of breast tumours. A similar regime is appropriate for the administration of a compound of formula I, most conveniently in the form of a pharmaceutical composition.

According to a further feature of the invention, there is provided a pharmaceutical composition comprising a compound of formula I or a pharmaceutically acceptable salt thereof together with a pharmaceutically acceptable diluent or carrier.

The composition may be in a form suitable for oral or parenteral administration. A tablet or capsule is a particularly convenient form for oral administration, and such a composition may be made by conventional methods and contain conventional excipients. Thus a tablet could contain diluents, for example a mannitol or maize starch, disintegrating agents, for example, alginic acid, binding agents, for example methylcellulose, and lubricating agents, for example magnesium stearate.

A composition for oral administration may conveniently contain from 5-50 mg. of a compound of formula I, preferably 5-20 mg.

The invention is illustrated but not limited by the following Examples:

EXAMPLE 1

A solution of 1-(p-β-dimethylaminoethoxypheny)-1-[p-(2-tetrahydropyranyloxy)phenyl]-2-phenylpropan-1-ol (3 g.) in ethanol (50 ml.) was acidified with concentrated hydrochloric acid and heated under reflux for 2 hours. The solvent was evaporated and the residue was stirred with water and made alkaline by the addition of ammonia solution. The precipitated base was extracted with ether, the ethereal extract was dried and evaporated to give a mixture of the isomers of 1-(p-β-dimethylaminoethoxyphenyl)-1-p-hydroxyphenyl-2-phenyl-prop-1-ene.

This mixture was stirred with chloroform (30 ml.) and the insoluble material was crystallised from acetone to give 1-(p-β-dimethylaminoethoxyphenyl)-cis-1-p-hydroxyphenyl-2-phenylprop-1-ene (500 mg.), m.p. 178°–180° C.

The chloroform solution was evaporated and the residue triturated with chloroform. The mixture was filtered and the filtrate evaporated. The residue was crystallised from acetone to give 1-(p-β-dimethylaminoethoxyphenyl)-trans-1-p-hydroxyphenyl-2-phenylprop-1-ene (83 mg.), m.p. 140° C.

The propan-1-ol derivative used as starting material was prepared as follows:

2,3-Dihydropyran (4.6 g.) and a few crystals of toluene-p-sulphonic acid were added to a solution of 4-hydroxy-α-methyldesoxybenzoin (11.3 g.) in chloroform (100 ml.). The resulting solution was heated under reflux for 5 mins., cooled and washed with 5% w/v aqueous sodium bicarbonate solution. The chloroform solution was then dried and evaporated, and the residue crystallised from acetone to give 4-(2-tetrahydropyranyloxy)-α-methyldesoxybenzoin (5.93 g.), m.p. 94°–96° C.

A 1.2M-solution of n-butyl-lithium in pentane (21 ml.) was added under nitrogen to a solution of p-β-dimethylaminoethoxyphenyl bromide (4.88 g.) in ether (60 ml.). The mixture was cooled to −20° C. and a solution of 4-(2-tetrahydropyranyloxy)-α-methyldesoxybenzoin (6.2 g.) in dry ether (200 ml.) was added dropwise. The mixture was allowed to reach room temperature, and water (200 ml.) was then added. The organic layer was separated, and the aqueous layer was extracted with ether. The extract was combined with the organic layer, dried and evaporated. The residue was triturated with ether to give 1-(p-β-dimethylaminoethoxyphenyl)-1-[p-(2-tetrahydropyranyloxy)phenyl]-2-phenylpropan-1-ol (3.4 g.), m.p. 108°–110° C.

EXAMPLE 2

The procedure described in Example 1 was repeated using an alkanol derivative of the formula:

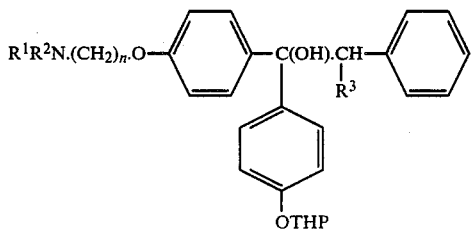

THP = 2-tetrahydropyranyl to give an alkene derivative of the formula:

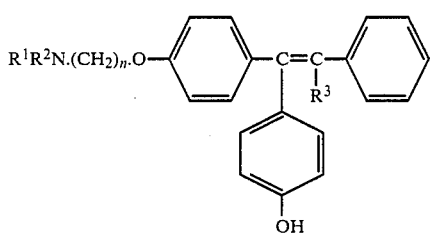

| R¹ | R² | n | R³ | isomer | m.p. °C. |
|---|---|---|---|---|---|
| Et | Et | 2 | Me | cis | 144–146 |
| Et | Et | 2 | Et | cis[1] | 168–170 |
| Me | Me | 3 | Et | cis[2] | 179–181 |

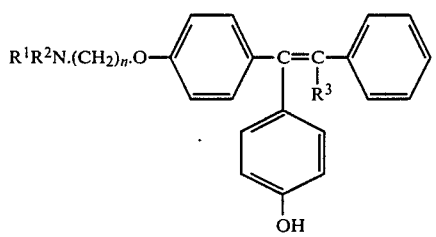

| R¹ | R² | n | R³ | isomer | m.p. °C. |
|---|---|---|---|---|---|
| Me | Me | 2 | isoPr | trans[3] | 152–153 |

[1]Separated from a mixture of the cis and trans isomers by chromatography on 20 × 20 × 0.2 cm³ silica plates (15 mg. per plate) developed twice in 10% v/v piperidine/toluene, R_F 0.61.
[2]Separated from a mixture of the cis and trans isomers by chromatography on silica (10 g. per 1000 g. of silica) eluted with 10% v/v piperidine/toluene, followed by extraction of the eluted material with boiling petrol (b.p. 80-100° C.) and crystallisation of the precipitated solid from toluene.
[3]Separated by trituration of crude mixture of isomers with acetone and crystallisation of the solid thus obtained from acetone.

The alkanols used as starting material were prepared as described in Example 1 using 4-(2-tetrahydropyranyloxy)-α-methyldesoxybenzoin, 4-(2-tetrahydropyranyloxy)-α-ethyl-desoxybenzoin (m.p. 82°–84° C.), or 4-(2-tetrahydropyranyloxy)-α-isopropyldesoxybenzoin (m.p. 109°–112° C.), butyllithium and p-β-diethylaminoethoxyphenyl bromide, p-γ-dimethylaminopropoxyphenyl bromide or p-β-dimethylaminoethoxyphenyl bromide, to give oils used without further purification.

EXAMPLE 3

A solution of 1-(p-β-dimethylaminoethoxyphenyl)-1,2-di-p-hydroxyphenylbutan-1-ol (900 mg.) in ethanol (90 ml.) was acidified with concentrated hydrochloric acid and heated under reflux for 3 hours. The solvent was evaporated and the residue was made alkaline by the addition of ammonia solution. The precipitated solid was crystallised from acetone to give 1-(p-β-dimethylaminoethoxyphenyl)-trans-1,2-di-p-hydroxyphenylbut-1-ene (37 mg.), m.p. 250°–252° C.

The butan-1-ol derivative used as starting material was prepared as follows:

A mixture of 4,4'-dihydroxy-α-ethyldesoxybenzoin (4.26 g.), sodium carbonate (4.8 g.), potassium iodide (0.15 g.) and benzyl chloride (4.57 g.) in ethanol (35 ml.) and water (5 ml.) was stirred and heated under reflux for 8 hours. The mixture was cooled, filtered, and the residue washed with water and recrystallised from petrol (b.p. 100°–120° C.) to give 4,4'-dibenzyloxy-α-ethyldesoxybenzoin, m.p. 84° C.

A 1.55 M-solution of n-butyl-lithium in hexane (16 ml.) was added under nitrogen to a solution of p-β-dimethylaminoethoxyphenyl bromide (4.88 g.) in tetrahydrofuran (50 ml.). The mixture was cooled to −20° C. and a solution of 4,4'-dibenzyloxy-α-ethyldesoxybenzoin (8.72 g.) in tetrahydrofuran (75 ml.) was added. The mixture was allowed to reach room temperature, and water (100 ml.) was then added. The organic layer was separated and the aqueous layer was extracted with ether. The extract was combined with the organic layer, dried and evaporated. The residue was crystallised from petrol (b.p. 80°–100° C.) to give 1-(p-β-dimethylaminoethoxyphenyl)-1,2-di-p-benzyloxyphenylbutan-1-ol, m.p. 119° C.

A solution of this butan-1-ol derivative (1.8 g.) in ethanol (180 ml.) was shaken with hydrogen in the presence of a 10% palladium-on-carbon catalyst. When no more hydrogen was absorbed, the mixture was filtered and the filtrate evaporated. The residue was triturated with ethyl acetate to give 1-(p-β-dimethylaminoethoxyphenyl)-1,2-di-p-hydroxyphenylbutan-1-ol (1.2 g.) as a solid.

EXAMPLE 4

Tablets were made by granulating a mixture of 1-(p-β-dimethylaminoethoxyphenyl)-trans-1-p-hydroxyphenyl-2-phenylprop-1-ene or its citrate with mannitol and maize starch in the presence of alginic acid and then mixing the dried granules with methylcellulose and magnesium stearate followed by compression into tablets. A typical tablet had the composition:

| | |
|---|---|
| Alkene derivative | 10 mg. |
| Mannitol | 111 mg. |
| Maize starch | 15 mg. |
| Alginic acid | 6 mg. |
| Methyl cellulose | 0.75 mg. |
| Magnesium stearate | 1.5 mg. |

In a similar manner, tablets were made using any other 1,1,2-triphenylalkene derivative described in any of Examples 1-3.

EXAMPLE 5

The procedure described in Example 1 was repeated using 1-(p-β-dimethylaminoethoxyphenyl)-1-[p-(2-tetrahydropyranyloxy)phenyl]-2-phenylpentan-1-ol as starting material to give 1-(p-β-dimethylaminoethoxyphenyl)-cis-1-p-hydroxyphenyl-2-phenylpent-1-ene, m.p. 126°-130° C.

The starting pentan-1-ol derivative was prepared as described in Example 1 from 4-(2-tetrahydropyranyloxy)-α-n-propyldesoxybenzoin (m.p. 79°-82° C.), butyllithium and p-β-dimethylaminoethoxyphenyl bromide.

EXAMPLE 6

A solution of 1(p-β-dimethylaminoethoxyphenyl)-1-[p-(2-tetrahydropyranyloxy)phenyl]-2-p-tolylbutan-1-ol (8.65 g.) in ethanol (100 ml.) was acidified with hydrochloric acid and heated under reflux for 3 hours. The solvent was evaporated, and the residue was made alkaline with ammonia solution. The resulting mixture was extracted with ethyl acetate, and the extract was dried and evaporated to give a mixture of the isomers of 1-(p-β-dimethylaminoethoxyphenyl)-1-(p-hydroxyphenyl)-2-p-tolylbut-1-ene (6.2 g.).

A mixture of the above mixed isomers (10 g.) and chloroform (100 ml.) was stirred and filtered, and the solid residue was crystallised twice from acetone. There was thus obtained 1-(p-β-dimethylaminoethoxyphenyl)-cis-1-p-hydroxyphenyl-2-p-tolylbut-1-ene (0.07 g.), m.p. 146°-148° C.

The chloroform filtrate was evaporated to dryness and the residue was stirred with chloroform (50 ml.). The mixture was filtered and the filtrate was evaporated to dryness. The residue was stirred with acetone (20 ml.) and the mixture was filtered. The solid residue was crystallised twice from acetone to give 1-(p-β-dimethylaminoethoxyphenyl)-trans-1-p-hydroxyphenyl-2-p-tolylbut-1-ene (0.25 g.), m.p. 184°-187° C.

The butan-1-ol derivative used as starting material was prepared as follows:

A solution of 4-β-dimethylaminoethoxy-4'-methyl-α-ethyldesoxybenzoin (6.5 g.) in ether (40 ml.) was added dropwise to a cooled solution of 4-(2-tetrahydropyranyloxy)phenyl magnesium bromide, obtained from 4-(2-tetrahydropyranyloxy)bromobenzene (5.94 g.) in tetrahydrofuran (40 ml.) and magnesium (1.1 g.) in dry ether (40 ml.). The resulting mixture was stirred and heated under reflux for 2 hours, and then a saturated aqueous solution of ammonium chloride (50 g.) was added. The organic layer was separated and the aqueous layer was extracted with ether. The organic layer and the ethereal extracts were combined and extracted with 5% w/v aqueous acetic acid (3×100 ml.). The extract was filtered and made alkaline with ammonia solution. The precipitated base was extracted with ether, and the extract dried and evaporated to give 1-(p-β-dimethylaminoethoxyphenyl)-1-[p-(2-tetrahydropyranyloxy)phenyl]-2-p-tolylbutan-1-ol as an oil.

EXAMPLE 7

The procedure described in Example 6 was repeated using an alkanol derivative of the formula:

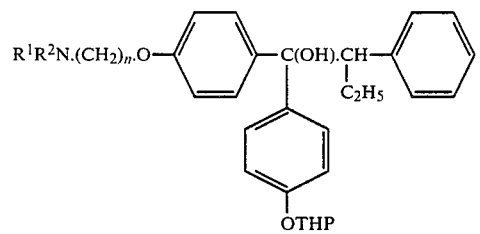

THP = 2-tetrahydropyranyl to give an alkene derivative of the formula:

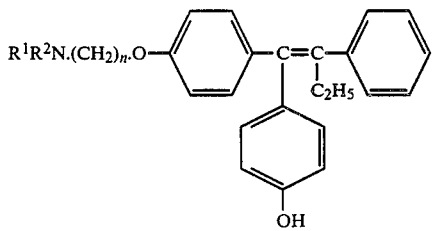

| $R^1$ | $R^2$ | n | isomer | m.p. (°C.) |
|---|---|---|---|---|
| | | 2 | trans | 160-162 |
| | | | cis | 138-140 |
| Me | Me | 4 | | 174 |
| Me | Me | 5 | cis | 168-172 |
| Et | Et | 3 | | 170-174 |

The alkanols used as starting material were prepared as described in Example 6 using 4-β-pyrrolidinoethoxy-α-ethyl-desoxybenzoin, b.p. 176°-182° C. at 0.025 mm., 4-δ-dimethylaminobutoxy-α-ethyldesoxybenzoin, 4-ε-dimethylaminopentyloxy-α-ethyldesoxybenzoin, or 4-γ-diethylaminopropoxy-α-ethyldesoxybenzoin, obtained by reacting the sodium salt of 4-hydroxy-α-ethyldesoxybenzoin with the corresponding aminoalkyl halide.

EXAMPLE 8

Tablets were made by granulating a mixture of 1-(p-β-dimethylaminoethoxyphenyl)-trans-1-(p-hydroxyphenyl)-2-p-tolylbut-1-ene or its citrate with mannitol and maize starch in the presence of alginic acid and then mixing the dried granules with methylcellulose and magnesium stearate followed by compression into tablets. A typical tablet had the composition:

| | |
|---|---|
| Alkene derivative | 10 mg. |
| Mannitol | 111 mg. |
| Maize starch | 15 mg. |
| Alginic acid | 6 mg. |
| Methyl cellulose | 0.75 mg. |
| Magnesium stearate | 1.5 mg. |

In a similar manner, tablets were made using any other 1,1,2-triphenylalkene derivative described in any of Examples 5–7.

EXAMPLE 9

The procedure described in Example 6 was repeated using the appropriate 1-(p-β-dimethylaminoethoxyphenyl)-1-[p-(2-tetrahydropyranyloxy)phenyl]-2-arylbutan-1-ol as starting material. There were thus obtained alkene derivatives of the formula:

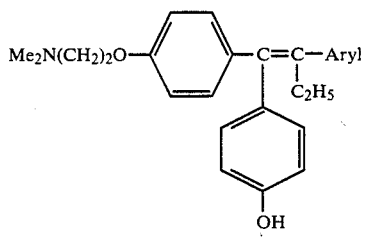

| Aryl | isomer | m.p. (°C.) | isomer separation procedure |
|---|---|---|---|
| p-chlorophenyl | cis | 149–151 | A |
| | trans | 157–159 | |
| m-chlorophenyl | cis | 95–97 | D |
| p-bromophenyl | cis | 119–121 | D |
| m-tolyl | trans | 172–174 | D |
| α-naphthyl | cis | 196–198 | A |
| | trans | 173–175 | |
| β-naphthyl | cis | 193–195 | A |
| | trans | 185–187 | |
| p-ethylphenyl | cis | 125 | B |
| | trans | 175 | |
| o-tolyl | cis | 170–171 | C |
| | trans | 180–181 | |

Procedure for separation of isomers

A. The solid mixture of isomers was triturated with petroleum ether, the liquor discarded and the solid triturated with chloroform. The solid residue was recrystallised twice from acetone to give the cis-isomer; the chloroform mother liquors were evaporated to dryness, the residue triturated with acetone and the solid residue crystallised twice from acetone to give the trans-isomer.

B. The mixture of isomers was triturated with acetone and the solid residue was crystallised from acetone to give the cis-isomer. The acetone mother liquors were evaporated to dryness and the residue crystallised from acetone to give the trans-isomer.

C. The mixture of isomers was crystallised from acetone to give the solid trans-isomer. The mother liquors from the crystallisation were absorbed into silica gel deactivated with 12% w/w water, and chromatographed on a similar column using a 1:3 v/v mixture of triethylamine and toluene, to give the cis isomers.

D. One isomer only appeared from crystallisation of the reaction mixture.

EXAMPLE 10

A solution of 4-dimethylaminoethoxy-α-ethyl-4'-fluorodesoxybenzoin (3.2 g.) in ether (30 ml.) was added to a stirred Grignard reagent prepared from a solution of p-methoxymethoxybromobenzene (3.25 g.) in tetrahydrofuran (30 ml.) and a suspension of magnesium (0.36 g.) in ether (30 ml.), and the mixture was heated under reflux for 2 hours, cooled and decomposed by the addition of a solution of ammonium chloride (30 g.) in water (100 ml.). The organic layer was separated, the aqueous layer was extracted with ether and the combined organic solutions were dried and evaporated to dryness.

The residue was stirred for 16 hours with isopropanol (20 ml.) which contained sufficient aqueous 10N-hydrochloric acid to give pH1, and the mixture was then evaporated to dryness. The residue was stirred with water and the mixture was made alkaline with concentrated aqueous ammonium hydroxide solution and then extracted with ether. The ethereal solution was extracted twice with 5% aqueous acetic acid (100 ml. each time) and the combined acidic extracts were treated with charcoal and filtered, and the filtrate was made alkaline with concentrated aqueous ammonium hydroxide solution and extracted with ether. The extract was dried and evaporated to dryness and the residue triturated with acetone. The solid product was crystallised from acetone to give 1-(p-β-dimethylaminoethoxyphenyl)-cis-1-p-hydroxyphenyl-2-p-fluorophenylbut-1-ene, m.p. 172°–174° C.

The acetone mother liquor was evaporated to dryness and the residue was crystallised from acetone to give 1-(p-β-dimethylaminoethoxyphenyl)-trans-1-p-hydroxyphenyl-2-p-fluorophenylbut-1-ene, m.p. 152°–154° C.

Preparation of Starting Materials

A. The butanol starting materials were obtained by the series of reactions shown on the accompanying Flow-Sheet A. Detailed conditions are exemplified by those given below for the preparation of the compound wherein "Aryl" is β-naphthyl.

A solution of β-naphthylacetic acid (25 g.) in chloroform (25 ml.) was added to a solution of thionyl chloride (50 ml.) in chloroform (80 ml.) and the mixture was heated under reflux for 1 hour, cooled and evaporated to dryness. The solid residue was crystallised from petroleum ether (b.p. 80°–100° C.) to give β-naphthylacetyl chloride, m.p. 67°–70° C.

A solution of the above compound (19.4 g.) in dry 1,2-dichloroethane was added during 10 minutes to a stirred mixture of anhydrous alumminium chloride (14.66 g.), anisole (10.66 g.) and dry 1,2-dichloroethane (60 ml.) which had been cooled below 10° C., the temperature of the reaction mixture being kept below 30° C. The mixture was then stirred for 1 hour at 50° C. and then cooled and poured into a mixture of ice (110 g.) and concentrated aqueous hydrochloric acid (40 ml.). The mixture was extracted with chloroform and the extract dried and evaporated to dryness. The residue was crystallised from toluene to give p-methoxyphenyl β-naphthylmethyl ketone, m.p. 132°–134° C.

FLOW-SHEET A

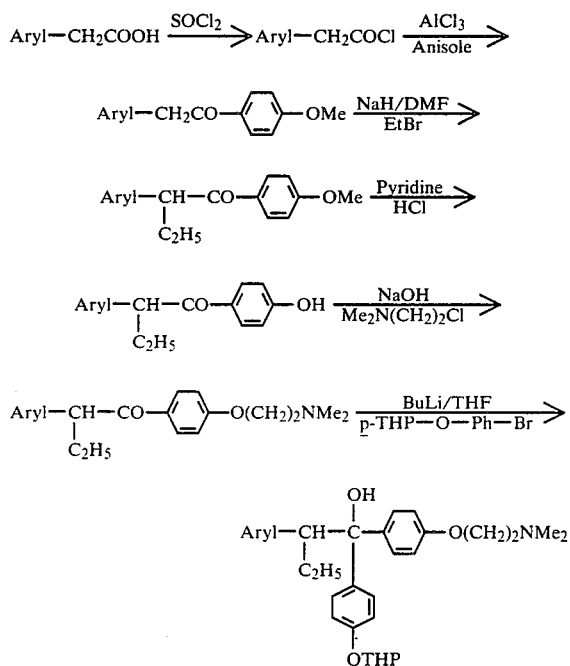

A solution of the above ketone (22.5 g.) in dimethylformamide (120 ml.) was added dropwise to a stirred suspension of sodium hydride (3.83 g. of a 63.9% dispersion in oil) in dimethylformamide (80 ml.) and the mixture was stirred for 1 hour at 60° C. and then cooled to laboratory temperature. A solution of ethylbromide (11.6 g.) in dimethylformamide (25 ml.) was added and the mixture was stirred for 2 hours and then poured into water (400 ml.). The mixture was extracted twice with ether and the extracts were dried and evaporated to dryness. The residue was purified (to remove unwanted 1-ethoxy-1-p-methoxyphenyl-2-β-naphthylethylene by-product) by chromatography on dry silica gel (1.6 kg., previously deactivated with water and equilibrated with the eluant) using a 9:1 v/v mixture of toluene and ethyl acetate as eluant. There was thus obtained p-methoxyphenyl 1-β-naphthylpropyl ketone as an oil.

Pyridine hydrochloride was prepared by adding concentrated aqueous hydrochloric acid (29 ml.) to pyridine (26 ml.) and distilling off volatile material until vapour temperature reached 210° C. It was then cooled to 140° C. and poured onto the above ketone (13.1 g.), and the mixture was heated under reflux for 30 minutes, cooled and poured onto ice (300 g.). The mixture was extracted three times with ether (100 ml. each time) and the combined extracts were extracted three times with aqueous 2N-sodium hydroxide solution (100 ml. each time). The alkaline extract was cooled, acidified with concentrated aqueous hydrochloric acid and extracted with ether and the extract was dried and evaporated to dryness. The residual oil was triturated with petroleum ether (b.p. 40°–60° C.) and the solid residue was crystallised from petroleum ether (b.p. 80°–100° C.) to give p-hydroxyphenyl 1-β-napthylpropyl ketone, m.p. 79°–81° C.

A solution of sodium hydroxide (1.27 g.) in water (5 ml.) was added to a stirred suspension of the above ketone (9.2 g.) in toluene (150 ml.) and the mixture was stirred and heated under reflux until all the water had been removed using a Dean and Stark separator. The mixture was cooled and a solution of β-dimethylaminoethyl chloride in toluene (prepared from 5.48 g. of β-dimethylaminoethyl chloride hydrochloride dissolved in water, basified with aqueous sodium hydroxide solution, extracted three times with 75 ml. each time of toluene and the toluene solution dried for 5 minutes over potassium hydroxide pellets) was added. The mixture was heated under reflux for 8 hours, cooled and filtered and the filtrate was evaporated to dryness. The residue was dissolved in ether and the solution was extracted three times with 5% aqueous acetic acid (90 ml. each time). The combined extracts were basified with aqueous sodium hydroxide solution and the mixture was extracted three times with ether (100 ml. each time). The combined extracts were dried and evaporated to dryness, the residue was triturated with petroleum ether (b.p. 40°–60° C.) and the solid residue was crystallised from petroleum ether (b.p. 60°–80° C.) to give p-β-dimethylaminoethoxyphenyl 1-β-naphthylpropyl ketone, m.p. 76°–78° C.

A solution of the above ketone (3.5 g.) in tetrahydrofuran (15 ml.) was added dropwise to a stirred mixture of p-(2-tetrahydropyranyloxy)bromobenzene (2.49 g. m.p. 58°–60° C., prepared from p-bromphenol and dihydropyran by a similar procedure to that described in the fourth paragraph of Example 1) and n-butyl-lithium (7.5 ml. of a 1.6 molar solution in pentane) in tetrahydrofuran (20 ml.) which had been prepared under an atmosphere of argon at −40° C. and stirred for 30 minutes at −20° C. The mixture was allowed to warm up to laboratory temperature during 16 hours, and was then cooled in an ice-bath and water (80 ml.) was added dropwise. The organic layer was separated, the aqueous layer was extracted with ether and the combined organic solutions were extracted three times with 5% aqueous acetic acid (80 ml. each time). The combined extracts were basified with aqueous ammonium hydroxide solution and the mixture was extracted three times with ether (50 ml. each time). The extract was dried and evaporated to dryness and the residual oil, which consisted of 1-p-(2-tetrahydropyranyloxy)phenyl-1-p-(β-dimethylaminoethoxy)phenyl-2-β-naphthylbutan-1-ol, was used without further purification.

Intermediates which were characterised by melting point are as follows:

Arylmethyl p-methoxyphenyl ketones

| Aryl | m.p. (°C.) |
|---|---|
| α-naphthyl | 137–139 |
| p-chlorophenyl | 132–135 |
| m-chlorophenyl | 64–66 |
| p-bromophenyl | 141–143 |
| m-tolyl | 62–64 |
| p-fluorophenyl | 108–110 |
| p-tolyl | 85–86 |

1-Arylpropyl p-hydroxyphenyl ketones

| Aryl | m.p. (°C.) |
|---|---|
| α-naphthyl | 108–110 |
| p-chlorophenyl | 95–98 |
| m-chlorophenyl | 88–90 |
| m-tolyl | 108–110 |

| Aryl | m.p. (°C.) |
|---|---|
| p-fluorophenyl | 102–104 |

B. The butanol starting materials were obtained by the series of reactions shown on the accompanying Flow-Sheet B, the last stage being identical with that described under A above. Detailed conditions are exemplified by those given below for the preparation of the compound wherein "Aryl" is p-ethylphenyl.

Concentrated aqueous hydrochloric acid (10 ml.) was added to a solution of p-β-dimethylaminoethoxybenzaldehyde (19.2 g.) and propane-1,3-dithiol (10.8 g.) in toluene (160 ml.) which was cooled in an ice-bath, and the mixture was then heated under reflux for 30 minutes, cooled and poured into saturated aqueous ammonium chloride solution (400 ml.). The mixture was adjusted to pH9 and extracted three times with ethyl acetate (100 ml. each time) and the combined extracts were washed with dilute aqueous sodium hydroxide solution, dried and evaporated to dryness. The residue was crystallised from aqueous ethanol to give dimethylaminoethoxyphenyl)-1,3-dithiane,

FLOW-SHEET B

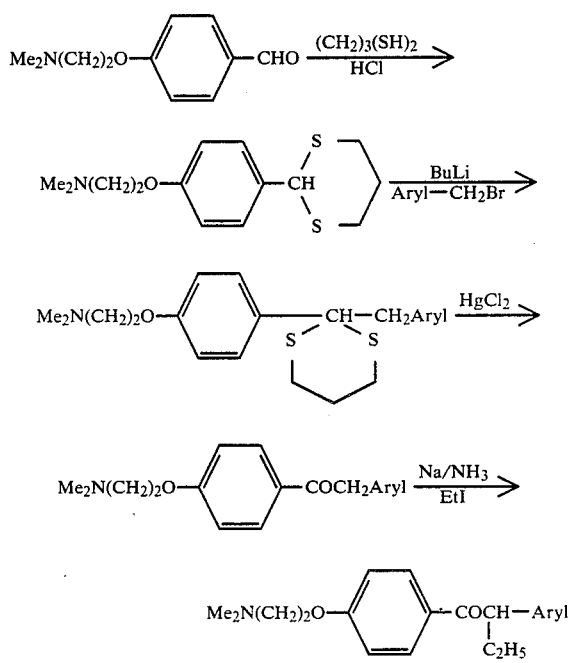

and then as under Flow-Sheet A n-Butyl-lithium (23.7 ml. of a 1.4 molar solution in hexane) was added to a stirred solution of the above dithiane (10 g.) in dry tetrahydrofuran (130 ml.) which was cooled to −70° C. under an atmosphere of nitrogen. The mixture was stirred for 5 minutes and p-ethylbenzylbromide (7.1 ml.; prepared from methyl p-ethylbenzoate by reduction with lithium alumminium hydride and then reaction with phosphorus tribromide) was then added and the mixture was allowed to warm up to laboratory temperature and was then poured into water (100 ml.). The mixture was extracted three times with methylene chloride (50 ml. each time) and the combined extracts were dried and evaporated to dryness. The residue was chromatographed on a dry column of silica gel (550 g., previously deactivated with water and equilibrated with eluant) using a 1:3 v/v mixture of triethylamine and toluene as eluant. There was thus obtained 2-(p-β-dimethylaminoethoxyphenyl)-2-ethylbenzyl-1,3-dithiane as an oil.

A solution of the above dithiane (4.6 g.) in acetonitrile (98 ml.) was added to a stirred mixture of mercuric chloride (6.5 g.), calcium carbonate (1.3 g.), acetonitrile (103.5 ml.) and water (11.5 ml.) and the mixture was stirred for 30 minutes. Methylene chloride (100 ml.) was added, the mixture was filtered and the filtrate dried and evaporated to dryness under reduced pressure. The residue was chromatographed on a dry column of silica gel in a similar manner to that described in the last paragraph above, and the product obtained was crystallised from hexane at −20° C. to give 4-β-dimethylaminoethoxy-4'-ethyldesoxybenzoin, m.p. 56° C.

A solution of the above desoxybenzoin (1.3 g.) in dry tetrahydrofuran (20 ml.) was added to a stirred solution of sodium (0.105 g.) in liqued ammonia (40 ml.) at −70° C., and the mixture was allowed to warm up to −30° C. during 15 minutes. Ethyl iodide (0.42 ml.) was added, the mixture was allowed to reflux at −20° C. for 2 hours, ammonium chloride (2.5 g.) was added and the ammonia was allowed to evaporate off. Water (100 ml.) was added, the mixture was extracted three times with hexane (50 ml. each time) and the combined extracts were dried and evaporated to dryness. The residual oil was chromatographed on a dry column of silica gel (205 g.) by a similar procedure to that described above, to give α,4'-diethyl-4-β-dimethylaminoethoxydesoxybenzoin as an oil.

This was reacted with p-(2-tetrahydropyranyloxy)-bromobenzene by a similar procedure to that described under A above.

Similarly, starting with o-methylbenzyl bromide a similar reaction sequence gave 4-β-dimethylaminoethoxy-α-ethyl-2'-methyldesoxybenzoin, the only characterised intermediate being 4-β-dimethylaminoethoxy-2'-methyldesoxybenzoin, m.p. 80°-81° C.

EXAMPLE 11

The process described in Example 1 was repeated using 1-(p-β-ethylaminoethoxyphenyl)-1-[p-(2-tetrahydropyranyloxy)phenyl]-2-phenylpropan-1-ol as starting material. The mixture of isomers thus obtained was triturated with petroleum ether (b.p. 40°-60° C.) and the solid residue thus obtained was crystallised from isopropanol to give 1-(p-β-ethylaminoethoxyphenyl)-cis-1-p-hydroxyphenyl-2-phenylprop-1-ene, m.p. 213°-215° C. The isopropanol mother liquors were evaporated to dryness and the residue was crystallised from acetone to give 1-(p-β-ethylaminoethoxyphenyl)-trans-1-p-hydroxyphenyl-2-phenylprop-1-ene, m.p. 134°-136° C.

The starting material was obtained by reacting 4-β-bromoethoxy-α-methyldesoxybenzoin with N-benzylethylamine in tetrahydrofuran, reacting the 4-β-(N-benzyl-N-ethylaminoethoxy)-α-methyldesoxybenzoin thus obtained with p-(2-tetrahydropyranyloxy)bromobenzene and n-butyl-lithium, followed by removal of the N-benzyl group by hydrogenolysis in ethanol solution over a 10% palladium-on-charcoal catalyst.

EXAMPLE 12

The process described in Example 1 was repeated using 1-(p-6-dimethylaminohexyloxyphenyl)-1-[p-(2- tetrahydropyranyloxy)phenyl]-2-phenylbutan-1-ol as starting material. The mixture of isomers thus obtained was triturated with petroleum ether (b.p. 40°-60° C.) and the solid residue was crystallised from acetone to give 1-(p-6-dimethylaminohexyloxyphenyl)-cis-1-p-hydroxyphenyl-2-phenylbut-1-ene, m.p. 165°–167° C.

The starting material was obtained by reacting 4-hydroxy-α-ethyldesoxybenzoin with 1,6-dichlorohexane in ethanol solution in the presence of potassium hydroxide, reacting the 4-(6-chlorohexyloxy)-α-ethyldesoxybenzoin thus obtained with dimethylamine in ethanol solution, and then reacting the 4-(6-dimethylaminohexyloxy)-α-ethyldesoxybenzoin thus obtained with p-(2-tetrahydropyranyloxy)bromobenzene and n-butyl-lithium.

EXAMPLE 13

Tablets were made by granulating a mixture of 1-(p-β-dimethylaminoethoxyphenyl)-trans-1-(p-hydroxyphenyl)-2-p-chlorophenyl-but-1-ene or its citrate with mannitol and maize starch in the presence of algininc acid and then mixing the dried granules with methylcellulose and magnesium stearate followed by compression into tablets. A typical tablet had the composition:

| | |
|---|---|
| Alkene derivative | 10 mg. |
| Mannitol | 111 mg. |
| Maize starch | 15 mg. |
| Alginic acid | 6 mg. |
| Methyl cellulose | 0.75 mg. |
| Magnesium stearate | 1.5 mg. | using any other 1,1,2-triphenylalkene derivative described in any of Examples 9–12.

What we claim is:

1. An alkene derivative of the formula:

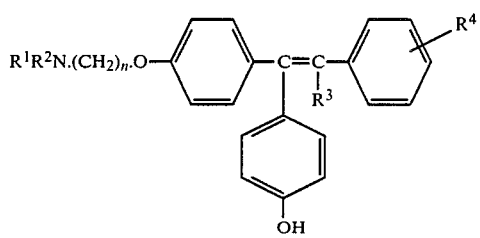

wherein either $R^1$ is a hydrogen atom or a lower alkyl radical and $R^2$ is a lower alkyl radical, or $R^1$ and $R^2$ are joined together with the adjacent nitrogen atom to form a heterocyclic radical; $R^3$ is a halogen atom or a lower alkyl radical; $R^4$ is a halogen atom, or a hydroxy or lower alkyl radical, or is the buta-1,3-dienyl radical such that together with the benzene ring it forms a naphthyl radical; and n is 2 or a pharmaceutically-acceptable acid-addition salt thereof.

2. An alkene derivative as claimed in claim 1 wherein $R^1$ and $R^2$ are both the same lower alkyl radical, wherein $R^3$ is a lower alkyl radical, wherein $R^4$ is a halogen atom or a lower alkyl radical, and wherein n is 2, or a pharmaceutically-acceptable acid-addition salt thereof.

3. An alkene derivative as claimed in claim 2 wherein $R^1$ and $R^2$ are both methyl radicals, $R^3$ is an ethyl radical, $R^4$ is a fluorine, chlorine or bromine atom or a methyl or ethyl radical, and n is 2, or a pharmaceutically-acceptable acid-addition salt thereof.

4. An alkene derivative as claimed in claim 3 wherein the substituent $R^4$ is in the 4-position of the benzene ring, or a pharmaceutically-acceptable acid-addition salt thereof.

5. A compound claimed in claim 1 selected from 1-p-β-dimethylaminoethoxyphenyl)-cis-p-hydroxyphenyl-2-p-tolylbut-1-ene, 1-(p-dimethylaminoethoxyphenyl)-trans-1-p-hydroxyphenyl-2-p-chlorophenylbut-1-ene, 1-p-β-dimethylaminoethoxyphenyl)-cis-1-p-hydroxyphenyl-2-p-chlorophenylbut-1-ene, 1-(p-β-dimethylaminoethoxyphenyl)-trans-1-p-hydroxyphenyl-2-p-fluorophenylbut-1-ene and 1-(p-β-dimethylaminoethoxyphenyl)cis-1-p-hydroxyphenyl-2-p-fluorophenyl-but-1-ene.

6. A pharmaceutical composition which comprises an alkene derivative or a pharmaceutically-acceptable acid-addition salt thereof, claimed in claim 1, together with a pharmaceutically-acceptable diluent or carrier.

7. A method for producing an antioestrogenic effect in a warm-blooded animal in need of such an effect which comprises administering to said animal an effective amount of an alkene derivative or a pharmaceutically-acceptable acid-addition salt thereof claimed in claim 1.

* * * * *